US00PP32826P2

(12) United States Plant Patent
Moon

(10) Patent No.: US PP32,826 P2
(45) Date of Patent: Feb. 23, 2021

(54) ***CARPINUS* TREE NAMED 'CCMTF2'**

(50) Latin Name: *Carpinus caroliniana*
Varietal Denomination: CCMTF2

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 16/602,872

(22) Filed: Dec. 13, 2019

(51) Int. Cl.
*A01H 5/00* (2018.01)
*A01H 6/00* (2018.01)

(52) U.S. Cl.
USPC ..... Plt./216

(58) Field of Classification Search
USPC ..... Plt./216
See application file for complete search history.

*Primary Examiner* — Susan McCormick Ewoldt
(74) *Attorney, Agent, or Firm* — Cassandra Bright

(57) ABSTRACT

A new and distinct *Carpinus caroliniana* tree named 'CCMTF2' is disclosed, characterized by a fastigiate form, clean leaf drop, recurved foliage with prominent veins. Trees produce red Fall foliage. The new variety is a *Carpinus* tree, typically used for landscapes and gardens.

3 Drawing Sheets

Latin name of the genus and species: *Carpinus caroliniana.*

Variety denomination: 'CCMTF2'.

BACKGROUND OF THE INVENTION

The new cultivar is a product of chance discovery. The new variety was discovered growing as a seedling among a group of (unknown) crossbred *Carpinus caroliniana* at a tree farm in Loganville, Ga. The inventor made this discovery in Spring 2014.

Asexual reproduction by grafting of the new cultivar 'CCMTF2' was first performed during the Summer of 2014 at a farm in Washington, Ga. The cleft grafting system developed by the inventor has resulted in progeny that have proven the characteristics of the new variety to be genetically stable. This grafting process involved taking cuttings in February, being grafted, and being placed in calloused chambers for approximately three weeks. They are then moved into 3"×6" tree band pots and placed in humidity chambers for approximately four weeks. Furthermore, these observations have confirmed that the new variety represents a new and improved variety of *Carpinus caroliniana* tree as particularly evidenced by the fastigiate form red leaves in the fall. These genetic traits can be consistently reproduced by asexual propagation.

SUMMARY OF THE INVENTION

The cultivar 'CCMTF2' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'CCMTF2' grown in Washington, Ga. These characteristics in combination distinguish 'CCMTF2' as a new and distinct *Carpinus caroliniana* cultivar:

1. Fastigiate form.
2. Medium vigor.
3. Leaf recurved and heavily ribbed.
4. Clean leaf drop.

PARENT COMPARISON

The exact parent varieties cannot be identified. characteristics, however, plants of the new cultivar 'CCMTF2' differ in the following:

1. The new variety produces Fall foliage which is red, the parent produces a yellow Fall foliage.
2. The new variety has a more upright, acute branching angles than the parent.

COMMERCIAL COMPARISON

Plants of the new cultivar 'CCMTF2' are similar to plants of *Carpinus caroliniana* 'CCSQU', U.S. Plant Pat. No. 11,280, in most horticultural characteristics, however, plants of the new cultivar 'CCMTF2' differ in the following;

1. The new variety has a tighter, denser growth habit.
2. The new variety produce Fall foliage which is red, this comparator produces yellow to dark orange Fall foliage.

Plants of the new cultivar 'CCMTF2' are similar to plants of the unpatented commercial variety, *Carpinus caroliniana* 'Uxbridge' in most horticultural characteristics, however, plants of the new cultivar 'CCMTF2' differ in the following;

1. The new variety has a narrower, denser growth habit.
2. The new variety produces red Fall foliage, this comparator produces red and orange foliage in the Fall.

Plants of the new cultivar 'CCMTF2' are similar to plants of the unpatented commercial variety, *Carpinus caroliniana* 'J.N. Globe' in most horticultural characteristics, however, plants of the new cultivar 'CCMTF2' differ in the following:

1. The new variety has a fastigiate form, this comparator has a compact globe form
2. The new variety produces red Fall foliage, this comparator produces orange red fall color
3. The new variety has a medium growth rate, this comparator is slow growing.

Plants of the new cultivar 'CCMTF2' are similar to plants of the unpatented commercial variety, *Carpinus caroliniana*

'JFS-KW6' in most horticultural characteristics, however, plants of the new cultivar 'CCMTF2' differ in the following:

1. The new variety has a much narrower, denser growth habit.
2. The new variety has a medium growth rate, this comparator is slow growing.

Plants of the new cultivar 'CCMTF2' are similar to plants of the unpatented commercial variety, *Carpinus caroliniana* 'J.N. Upright' in most horticultural characteristics, however, plants of the new cultivar 'CCMTF2' differ in the following:

11. The new variety has a narrower, denser growth habit.
2. The new variety produces red Fall foliage, this comparator produces red and orange foliage in the Fall.

Plants of the new cultivar 'CCMTF2' are similar to plants of the unpatented commercial variety, *Carpinus caroliniana* 'Pyramidalis' in most horticultural characteristics, however, plants of the new cultivar 'CCMTF2' differ in the following:

1. The new variety has a fastigiate form, this comparator is v-shaped with a rounded top Plants of the new cultivar 'CCMTF2' are similar to plants of the unpatented commercial variety, *Carpinus caroliniana* 'Stowe Cascade' in most horticultural characteristics, however, plants of the new cultivar 'CCMTF2' differ in the following:

1. The new variety has a fastigiate form, this comparator has an arching, weeping form

BRIEF DESCRIPTION OF THE PHOTOGRAPHS

The accompanying photograph in FIG. 1 illustrates a field of trees of the new variety during early Summer, foliage color and the natural tree shape are illustrated.

Figure 1:
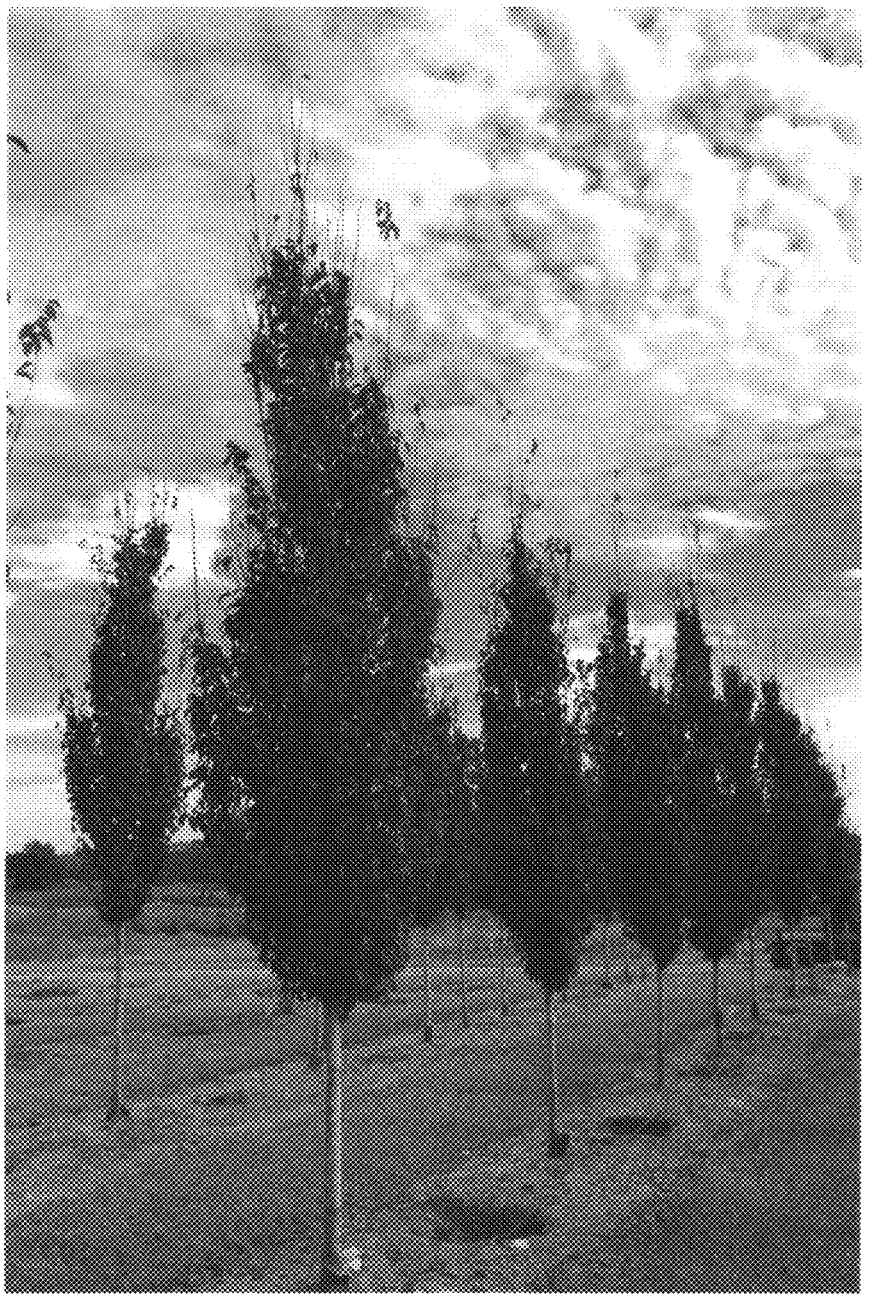
Figure 2:
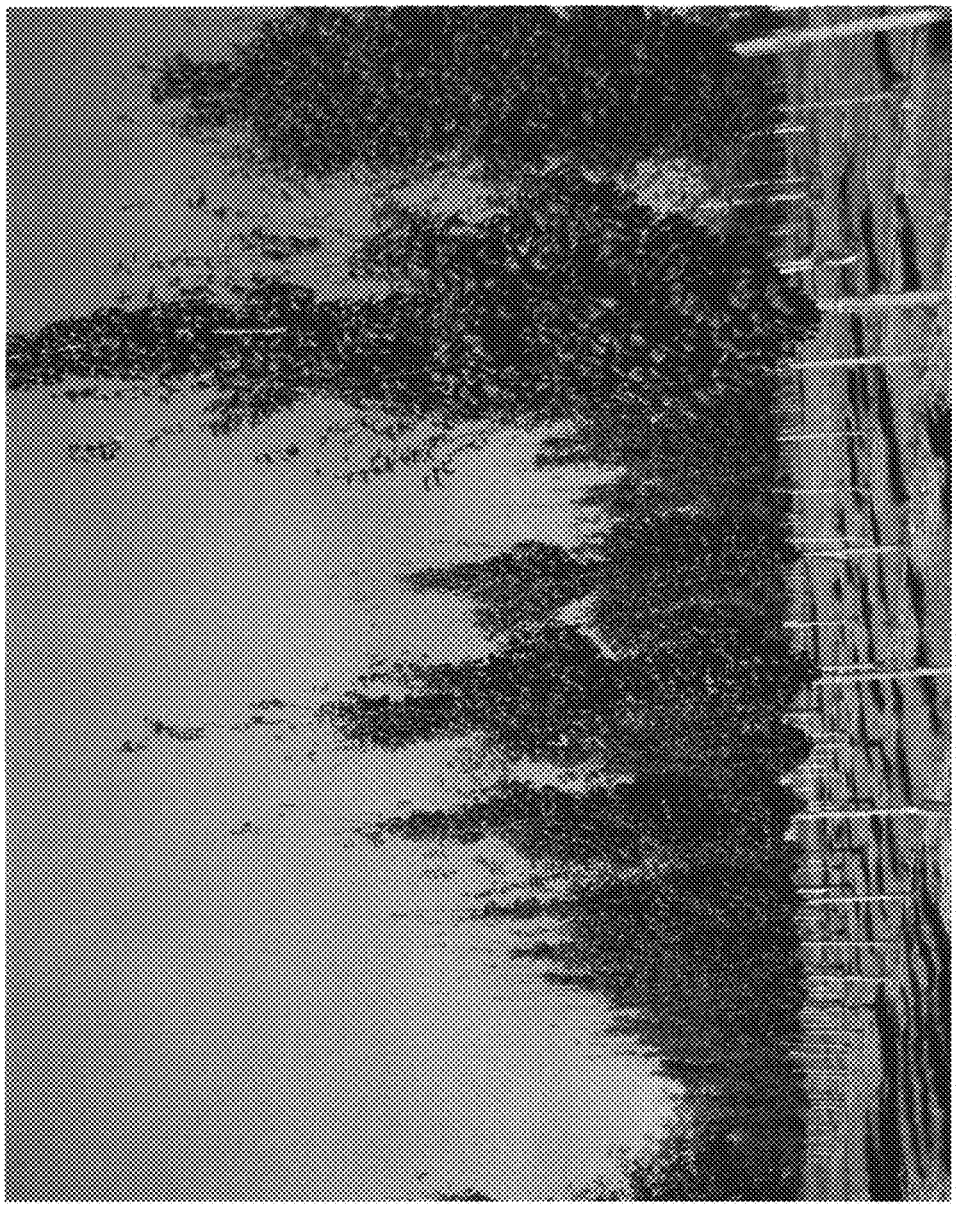
FIG. 2 illustrates a different view of the same field of 'CCMTF2'. Trees are approximately 4 years from planting into the field from a 3 gallon pot, 5 years old from grafting and grown in Washington, Ga.
Figure 3:
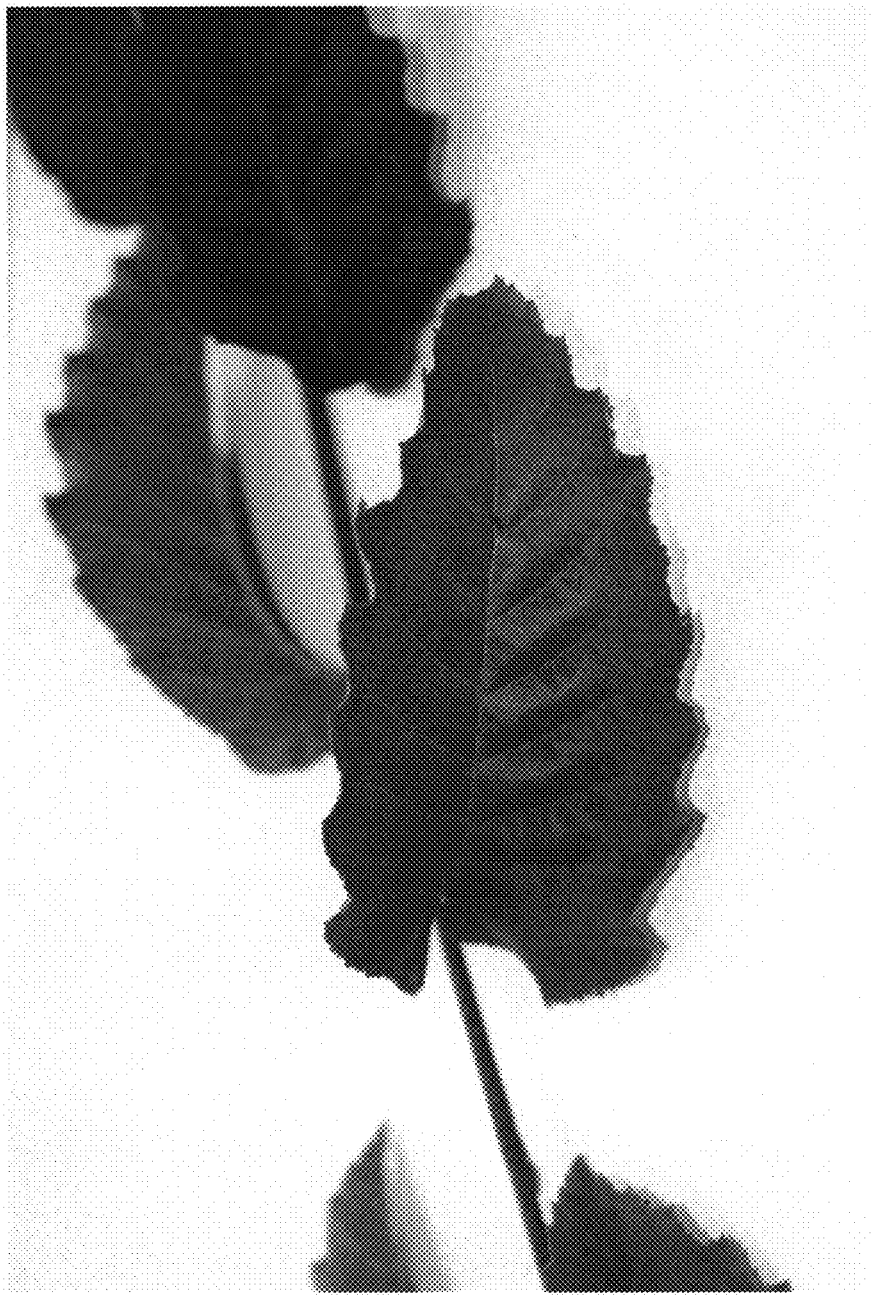
FIG. 3 illustrates a close-up view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'CCMTF2' plants grown outdoors and in a nursery in Washington, Ga. Plants are approximately 2 years old, in a 3 gallon nursery container. Temperatures ranged from 5° C. to 10° C. at night to 18° C. to 27° C. during the day. Measurements and numerical values represent averages of typical plant types.

Botanical classification: *Carpinus caroliniana* 'CCMTF2'.

Propagation: Cleft grafting.

Root description: Woody. Brown roots not accurately measured with an R.H.S. Colour chart.

Plant:

Growth habit: Fastigiate.

Height: About 10 feet at about 3 years.

Spread: About 3 feet at about 3 years.

Growth rate: Moderate.

Aspect and angle: Branches at acute angles, about 15 degrees.

Trunk characteristics:

*Diameter*.—About 3 inches measured at approximately 5 inches above soil level at 4 years.

*Color*.—Near RHS Greyed-Green 198A with large blotches 197A and 197B.

*Surface texture*.—Rippled.

*Lenticels present*.—Yes. Inconspicuous, round.

*Lenticel length*.—Less than 0.5 mm.

*Lenticel diameter*.—Less than 0.5 mm.

*Lenticel density*.—Moderate.

*Lenticel color*.—Near RHS Greyed-Green 198D.

Branch characteristics (at 2 years):

*Length*.—Average Range 25 to 50 cm.

*Diameter*.—Average 7 mm.

*Color*.—Near RHS Brown N200B with overlay Greyed-Purple 183A.

*Surface texture*.—Moderately dense lenticels, about 0.5 mm long and 0.5 mm wide. Colored near Greyed-Green 191D.

Foliage:

Leaf:

*Arrangement*.—Alternate.

*Shape*.—Ovate.

*Average length*.—Approximately 7 cm excluding petiole.

*Average width*.—Approximately 3.5 cm.

*Apex*.—Acute.

*Shape of blade*.—Asymmetrical broad deltate.

*Base*.—Obtuse or asymmetrical cordate.

*Margin*.—Double serrate. Secondary serration minute. Primary serration regular, at intervals about 5 to 7 mm.

*Aspect*.—Recurved.

*Texture of top surface*.—Glabrous.

*Texture of lower surface*.—Glabrous.

*Color*.—Young foliage: Upper side: Near RHS Yellow-Green 144B. Under side: Near RHS Yellow-Green 144B. Mature foliage: Upper side: Near RHS Green 137D. Under side: Near RHS Green 138A. Fall foliage: Upper side: Near RHS Red 45C. Under side: Near RHS Greyed-Red 180A.

*Venation*.—Type: Pinnate, prominent. Color: Venation color upper side: Near RHS Yellow-Green 145A. Venation color under side: Near RHS Yellow-Green N144B.

*Petiole*.—Length: Average 5 mm. Diameter: Average 2 mm. Color: upper side: Near RHS Yellow-Green 145A. under side: Near RHS Yellow-Green N144B.

Flower:

*Flowering begins*.—Around early Spring in Georgia. Individual male and female catkins.

*Male catkins*.—About 3 to 5 cm long, about 5 to 7 mm wide. Weeping. Colored near RHS Yellow-Green 145A, turning Yellow-Green 154C flushed Greyed-Red 183A.

*Female catkins*.—Paired, about 2 cm long and approximately 4 mm wide. Colored near Yellow-Green 149D.

Reproductive organs: Reproductive Organs minute, less than 1 mm and irregularly formed.

Androecium:

*Number*.—Typically 3 stamens per flower.

*Length*.—About 5 mm.

*Color*.—Near Yellow-Green 145C.

Gynoecium:

Pistil:

*Number.*—1.

*Length.*—9 mm.

*Style*.—Length: 5 mm. Color: Near Yellow-Green 154D.

*Stigma*.—Shape: Linear. Color: Near Greyed-Orange 163D.

Other characteristics:

Disease/pest resistance: Neither resistance nor susceptibility to normal diseases and pests of *Carpinus* has been observed.

Drought resistance: No tolerance for drought.

Temperature tolerance: USDA Zones 4 through 8.

Fruits: Ribbed nut enclosed in a drooping, papery 3-lobed involucre. Individual nuts about 6 mm long and 3 mm wide colored near Grey-Brown 199A. Involucre about 2 cm long and about 8 mm wide, colored Yellow-Green 144C when immature, changing to Green-Yellow 1B. Infructescence about 6 to 10 cm long.

What is claimed is:

1. A new and distinct cultivar of *Carpinus caroliniana* tree named 'CCMTF2' as herein illustrated and described.

* * * * *